US005879932A

United States Patent [19]

Van Erdewyk et al.

[11] Patent Number: 5,879,932

[45] Date of Patent: Mar. 9, 1999

[54] SLOW RELEASE MICROORGANISM DISPENSER

[76] Inventors: Michael Van Erdewyk, 7775 Grinnell Way, Lakeville, Minn. 55044; Vincent P. Spaulding, R.R. 1 Box 1236, Waymart, Pa. 18472

[21] Appl. No.: 931,541

[22] Filed: Sep. 16, 1997

[51] Int. Cl.$^6$ ..................... C12M 1/16

[52] U.S. Cl. ..................... 435/304.1; 435/299.2; 435/307.1; 435/309.1; 210/198.1; 422/265

[58] Field of Search ..................... 435/289.1, 297.1, 435/299.1, 299.2, 304.1, 304.2, 307.1, 309.1; 210/606, 608, 610, 615–617, 150, 198.1; 422/265

[56] References Cited

U.S. PATENT DOCUMENTS

| | | | |
|---|---|---|---|
| 2,826,484 | 3/1958 | Buehler | 23/267 |
| 2,934,409 | 4/1960 | Biehl | 23/267 |
| 3,792,979 | 2/1974 | Clinton | 23/267 A |
| 3,860,490 | 1/1975 | Guttag . | |
| 4,670,149 | 6/1987 | Francis | 210/608 |
| 4,692,314 | 9/1987 | Etani | 422/265 |
| 4,810,385 | 3/1989 | Hater et al. | 210/606 |
| 4,990,449 | 2/1991 | Caissel | 435/174 |
| 5,143,020 | 9/1992 | Patrick | 119/3 |
| 5,171,687 | 12/1992 | Moller et al. | 435/286 |
| 5,228,998 | 7/1993 | DiClemente et al. | 210/610 |
| 5,344,557 | 9/1994 | Scanzillo | 210/94 |
| 5,516,687 | 5/1996 | Perez et al. | 435/262 |
| 5,565,096 | 10/1996 | Phelan | 210/150 |

*Primary Examiner*—William H. Beisner
*Attorney, Agent, or Firm*—Haugen Law Firm PLLP

[57] ABSTRACT

A dispenser and method is provided for slowly releasing microorganisms into a surrounding body of fluid. The surrounding body of fluid may, for example, include a pond, lake, or waste management holding area. A major portion of the dispenser is submerged within the surrounding body of fluid and may be anchored in place to the bottom underlying the body of fluid. The dispenser includes a conically shaped flotation chamber and a spherical growth chamber. Microorganisms suspended in a gel are cultured within the growth chamber and then slowly release from the growth chamber into the surrounding body of fluid.

11 Claims, 5 Drawing Sheets

SLOW RELEASE MICROORGANISM DISPENSER

BACKGROUND OF THE INVENTION

I. Field of the Invention

This invention relates generally to a device and method to slowly release microorganisms into a body of fluid surrounding a major portion of the device. More particularly, this invention relates to a floating dispenser having microorganisms suspended in a gel within the dispenser, wherein the microorganisms multiply within the dispenser and slowly release into the outer body of fluid from a lower portion of the dispenser. A media contained within the dispenser provides a growth medium for the microorganisms within the dispenser.

II. Discussion of the Related Art

Over the years, microorganisms have been found useful in consuming undesirable matter such as algae, sludge, and the like. Generally, the microorganisms break down the undesirable matter into other more desirable chemical components. In order to maximize the effectiveness of the microorganisms, the microorganisms are slowly delivered into contact with the undesirable matter. When treating runoff ponds, holding ponds, lakes, etc., an anaerobic bacteria may be utilized to, in essence, feed off the algae and other biological matter suspended in the water.

Moller et al. in U.S. Pat. No. 5,171,687 describes an apparatus for culturing and delivering microbes for waste treatment in a flow system. Moller et al. utilizes solid microbial matter and nutrients in solid or gel form. The apparatus described by Moller et al. includes a complex two chamber system, requiring an electrical oxygen pump, valves, and other mechanical parts. These components add to the cost of the culturing and delivery system and further add to the complexity of the apparatus. Hence there is a need for an economical culturing and delivery device having a reduced number of parts. The present invention overcomes these and other disadvantages.

SUMMARY OF THE INVENTION

The purpose of the present invention is to provide a dispenser suitable for cultivating microorganisms suspended therein, such that the microorganisms later slowly release from the dispenser into a surrounding body of fluid. The dispenser includes a growth chamber having a plurality of conduits extending between an interior surface of the growth chamber and an external surface of the growth chamber. A growth media and nutrients are contained within the growth chamber. Prior to pouring the fluid suspending the microorganisms into the growth chamber, a plasticizer is added to the fluid to thereby form a gel substance, trapping the microorganisms within the gel. The gel is then poured into the growth chamber, whereby the microorganisms then attach and grow on an external surface of the media. In the preferred embodiment, the growth media comprises a plurality of spheres manufactured from a polymer having a density less than a density of water.

In the preferred embodiment, the dispenser is divided into an upper conical float chamber and a lower spherical growth chamber. The conical upper chamber provides stability to the device when floating in water and acts as a funnel, directing fluids, etc. towards the growth chamber. An open end is formed at the base of the conical floatation chamber and provides access to the hollow inner portion of the dispenser. A hook or tab extending from a lower portion of the growth chamber provides a means for securing the device to an anchor line or other tether.

In an alternate preferred embodiment, the dispenser comprises a tubular main body that is attached to a bottom portion of a common floatation device. The tubular main body includes a removable cap for filling the tubular body with media, nutrients and microorganisms suspended in liquid/gel. A plurality of ports provide an outlet for the microorganisms to slowly release out of the tubular body or growth chamber. A flange or rail extends from an upper surface of the tubular main body and is adapted for attaching to a lower surface of the floatation device.

OBJECTS

It is accordingly a principal object of the present invention to provide an economical dispenser and method for both cultivating microorganisms suspended within the dispenser and slowly releasing the microorganism from the dispenser;

Another object of the present invention is to provide a container divided into an upper and lower region, wherein the upper region defines a float chamber and the lower region defines a growth chamber;

Still another object of the present invention is to provide a container for growing and slowly releasing microorganisms therefrom into a surrounding fluid, wherein the container includes a media that increases the total surface area available for microorganism growth; and A further object of the present invention is to provide a means for recharging a growth chamber of the dispenser without removing the dispenser from the field placement.

These and other objects, as well as these and other features and advantages of the present invention will become readily apparent to those skilled in the art from a review of the following detailed description of the preferred embodiment in conjunction with the accompanying claims and drawings in which like numerals in the several views refer to corresponding parts.

DETAILED DESCRIPTION OF THE PREFERRED EMBODIMENT

Figure 2:
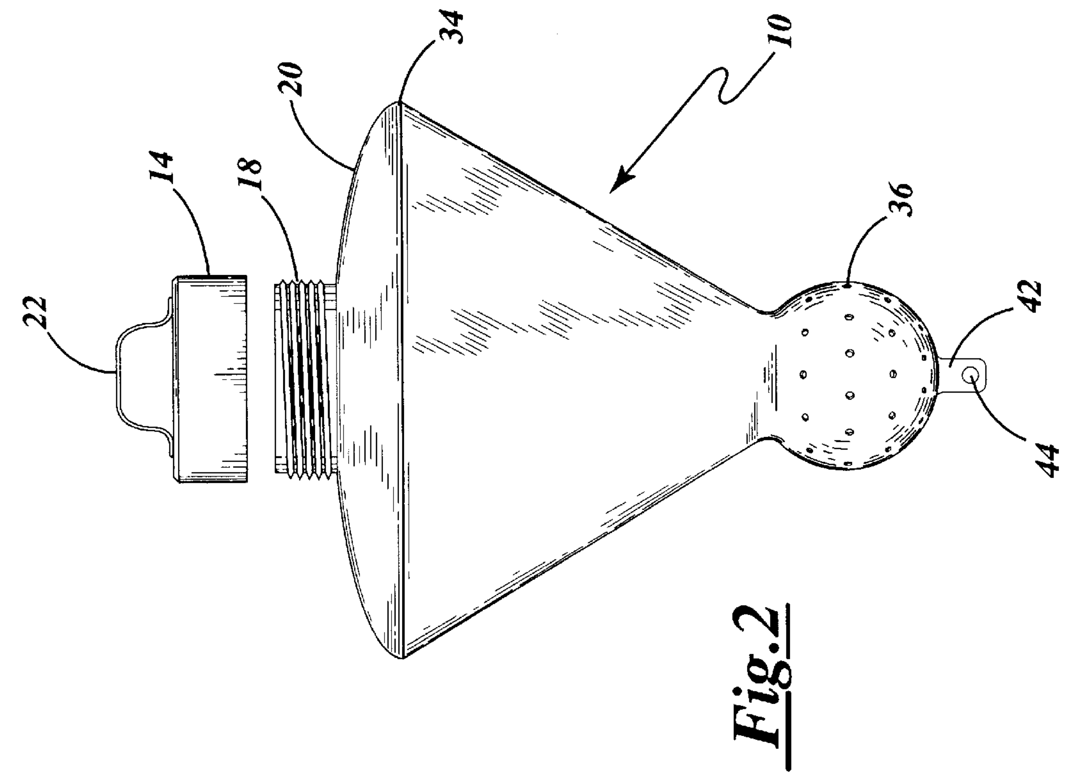
FIG. 2 is a partial exploded side elevational view of a microorganism dispenser of the type shown in FIG. 1.
Figure 1:
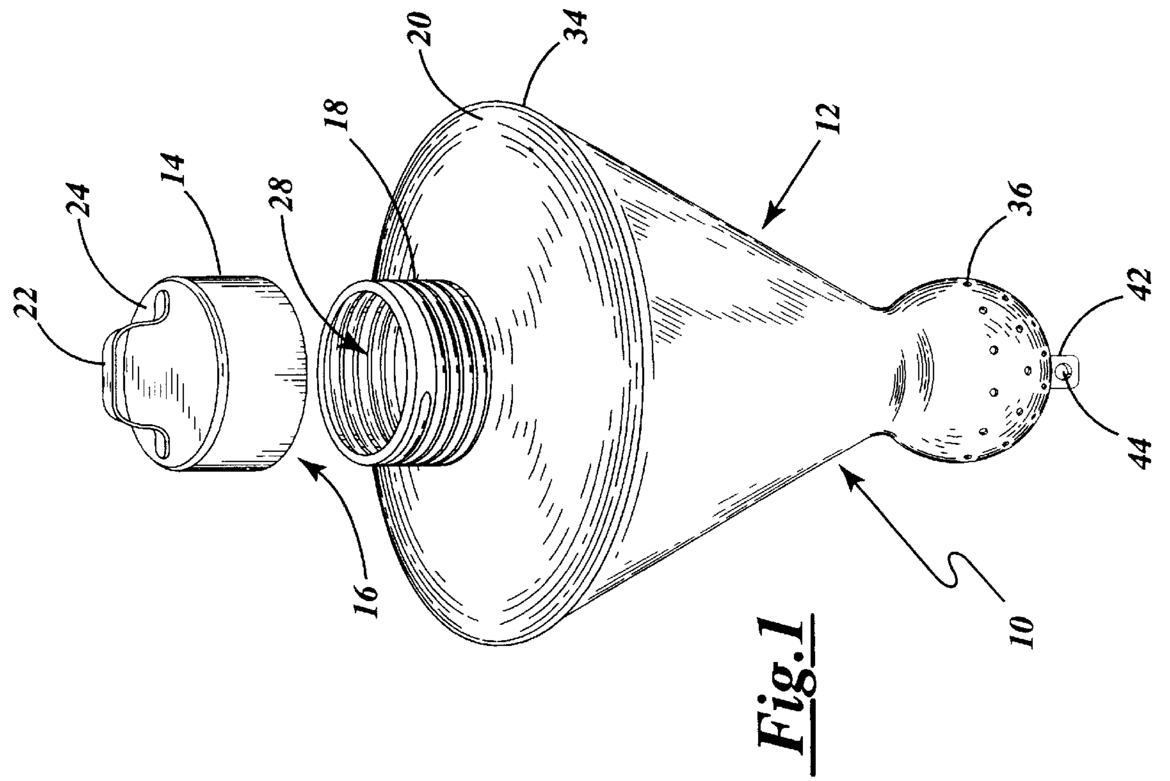
FIG. 1 is a partial exploded perspective view of the microorganism dispenser of the present invention.

Referring first to FIGS. 1 and 2, there is shown generally a microorganism dispenser 10 of the present invention. The dispenser 10 includes a main body portion 12 and a cap 14. The cap 14 includes internal threading 16 to securely screw onto a neck 18 extending from an upper portion 20 of the external main body 12. The cap 14 further includes a handle 22 extending from an upper surface 24 of the cap 14. When the cap 14 is secured to the main body 12, the user may carry the dispenser 10 by the handle 22. Also, when the dispenser 10 is submerged in water, for example, the dispenser 10 is easily pulled from the water by the handle 22. The cap 14 further includes a encapsulated air chamber protruding down from the handle. This chamber is to provide bouyancy and verticle stability.

Figure 4:
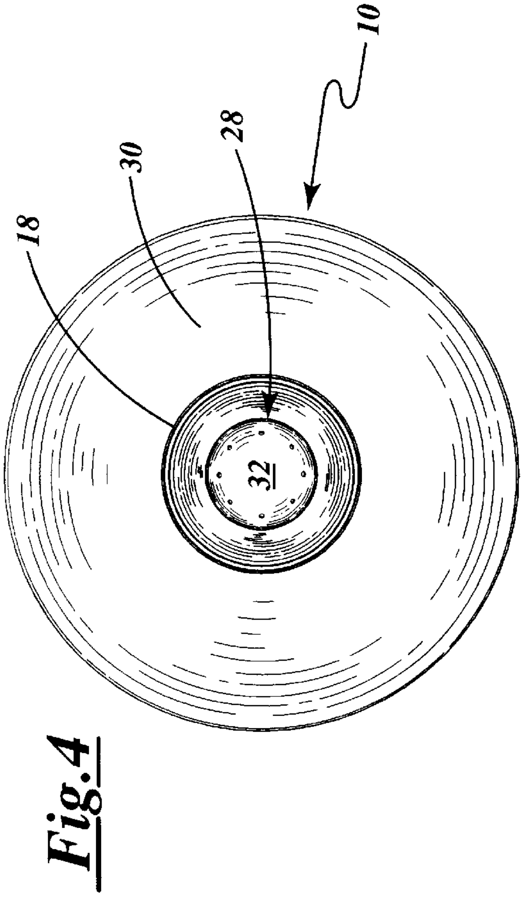
FIG. 4 is a top plan view of the dispenser of the type shown in FIG. 1 with the upper fill cap removed.
Figure 3:
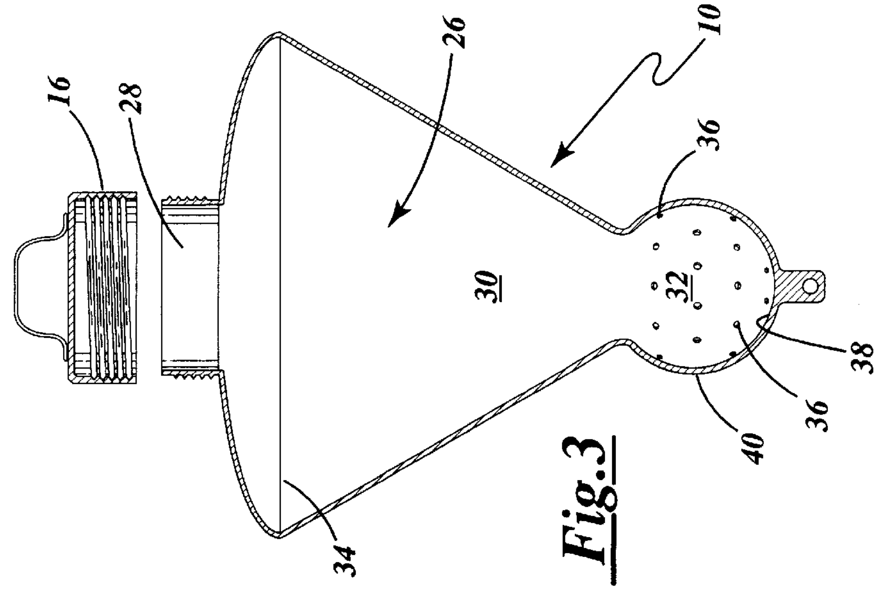
FIG. 3 is a partial sectional exploded view of the dispenser of the type shown in FIG. 1.

The main body 12 has a hollow interior 26 with an opening 28 formed in the neck 18 (see FIG. 3 and 4). The main body 12 generally comprises an upper flotation chamber 30 and a lower growth chamber 32. The upper floatation chamber 30 is in the shape of an inverted cone, having the base 34 of the cone forming the upper portion 20 of the main body 12. The sides of the upper floatation chamber 30 taper to the intersection with the growth chamber 32, thereby providing a self centering dispenser, when the dispenser is floating in a fluid, and adds to the buoyancy of the dispenser. The inner sidewall of the floatation chamber 30 also tapers toward the growth chamber 32, such that fluids within the flotation chamber 30 funnel down into the growth chamber 32.

Figure 5:
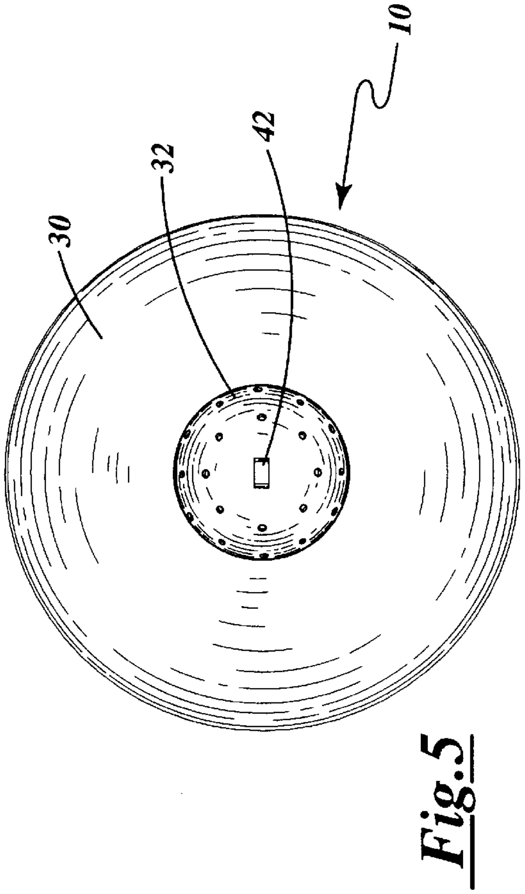
FIG. 5 is a bottom plan view of the dispenser of the type shown in FIG. 1.

The growth chamber 32 is spherical in shape and includes a plurality of ports 36 extending from an inner 38 to an outer 40 surface of the growth chamber 32. Those skilled in the art will appreciate that the size and number of ports 36 may be varied, to control the rate the gel drains from the sphere 32. Extending from a lower portion of the sphere 32 is a tab 42 having a bore 44 extending therethrough. The tab 42 is adapted for receiving an anchor line (not shown), such that the dispenser 10 may be anchored to the bottom of the body of fluid it is positioned within (see FIGS. 3 and 5).

Microorganisms suspended in a liquid/gel, growth media, and nutrients are all contained within the growth chamber 32. The microorganisms suspended in liquid/gel, growth media and nutrients are all available from Bioverse, Inc. of Eden Prairie, Minn. The microorganisms suspended in liquid is sold under the trademark AQUA-FORCE. The AQUA-FORCE includes a bacteria that, when combined with a plasticizer forms a gel, whereby the bacteria suspended in the gel attach to the media and grow on the media until being released out of the growth chamber. A growth media of suitable construction is available from Landtec Products, Inc., Agoura Hills, Calif. and sold under the mark Q-PAC. Without any limitation intended, the growth media may be manufactured from a polymer in a variety of sizes and shapes including fibers, spheres, pellets, and rods, spheres being preferred. Use of spherical shaped media is believed to maximize the surface area for bacteria growth. The density of the material used to manufacture the media may be varied depending upon the buoyancy desired. The spherical shape of the growth chamber 32 effectively contains the media within the growth chamber 32 when the dispenser 10 tips from side to side and further eliminates corners that may trap media therein.

Figure 6:
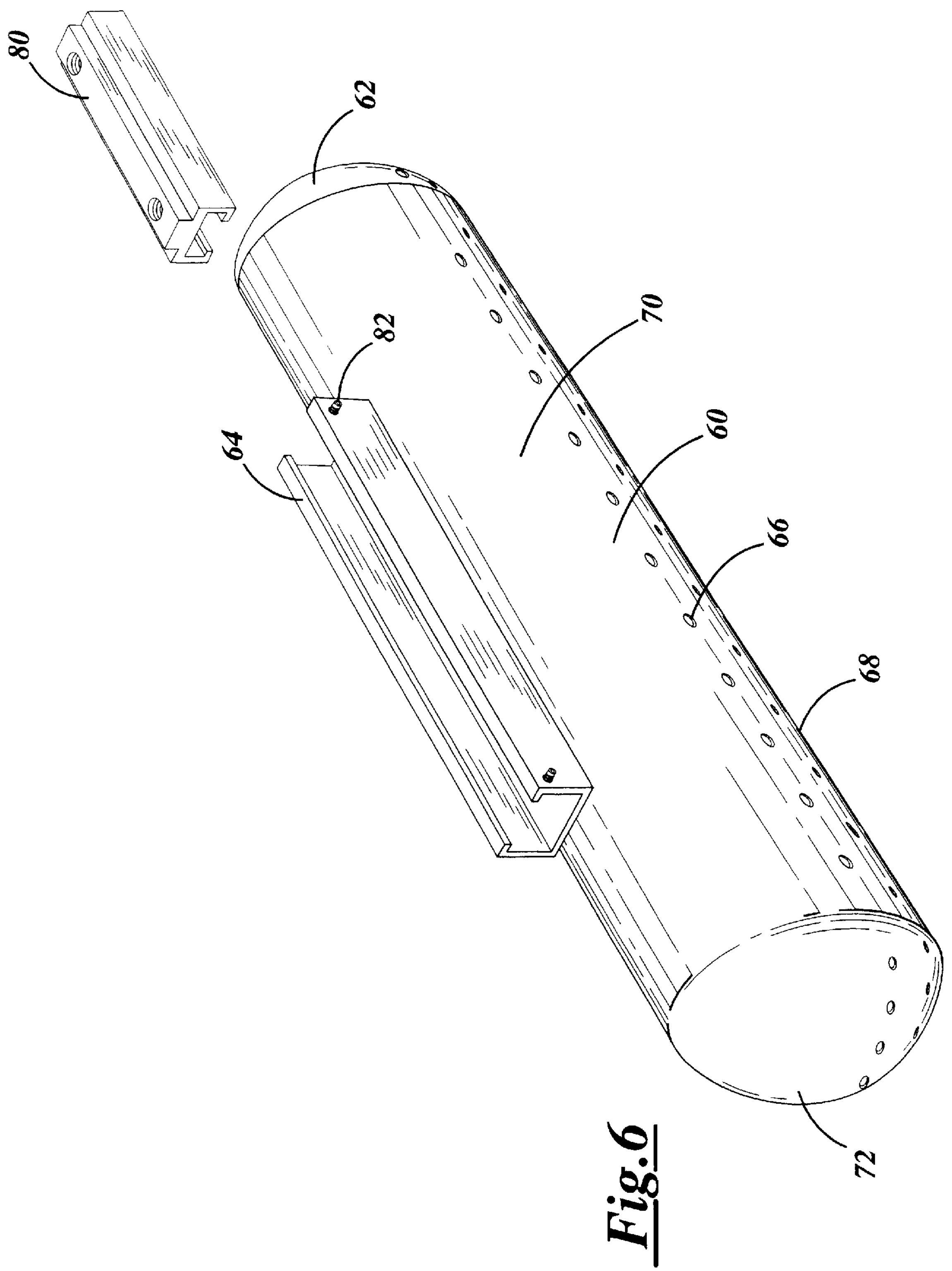
FIG. 6 is an exploded perspective view of an alternate embodiment of the microorganism dispenser of the present invention.
Figure 7:
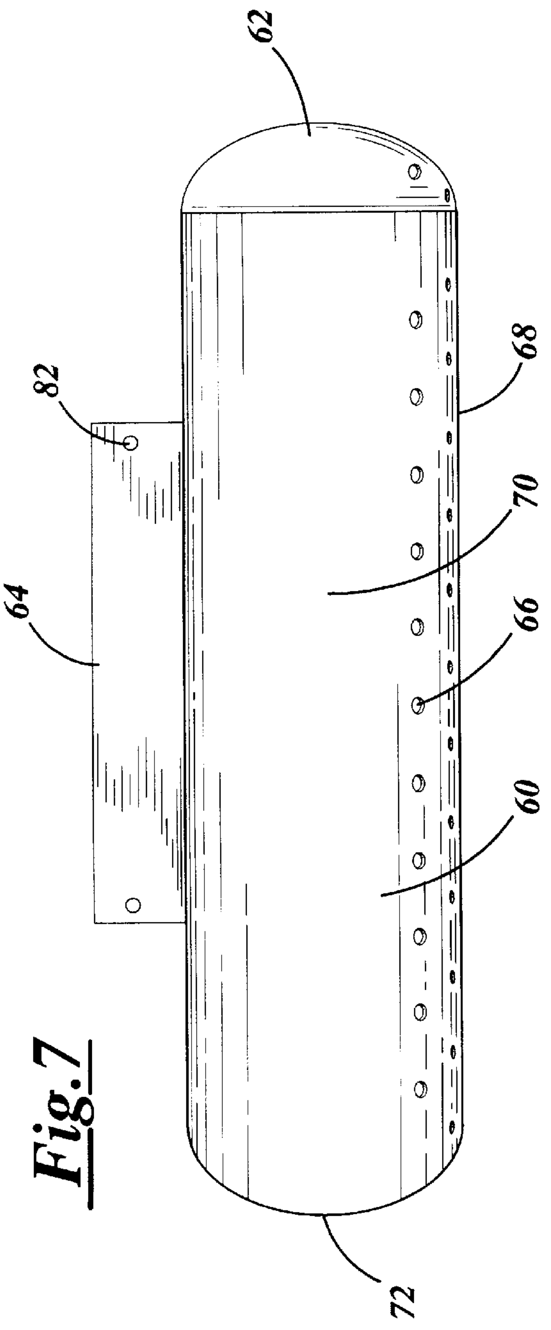
FIG. 7 is a side elevational view of the dispenser of the type shown in FIG. 6.
Figure 9:
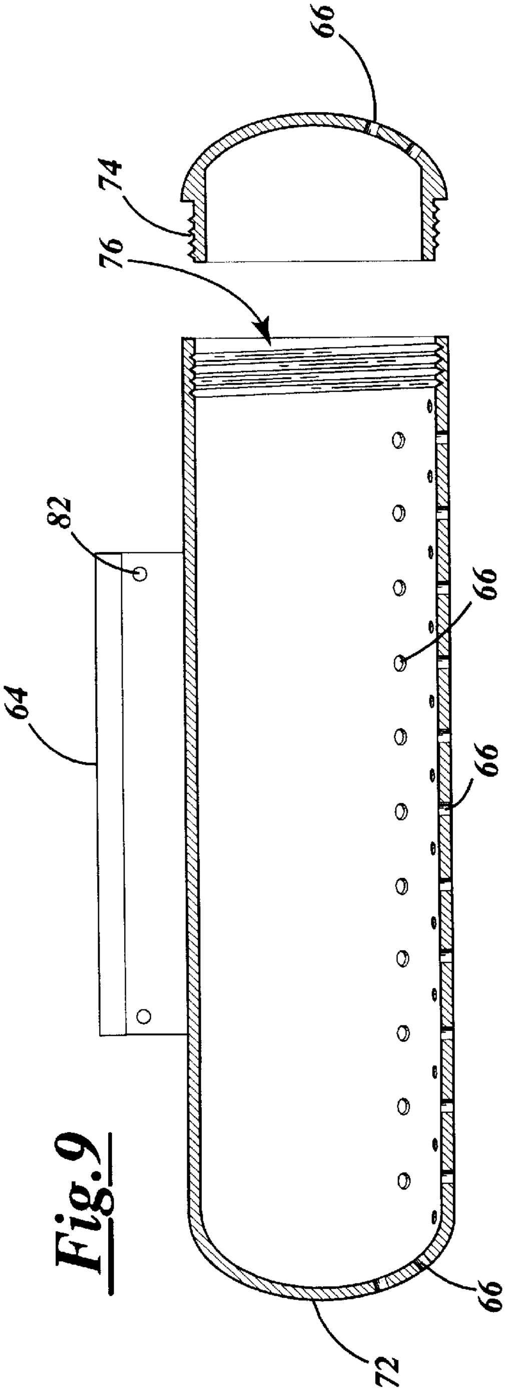
FIG. 9 is a partial sectional exploded view of the dispenser of the type shown in FIG. 6.
Figure 10:
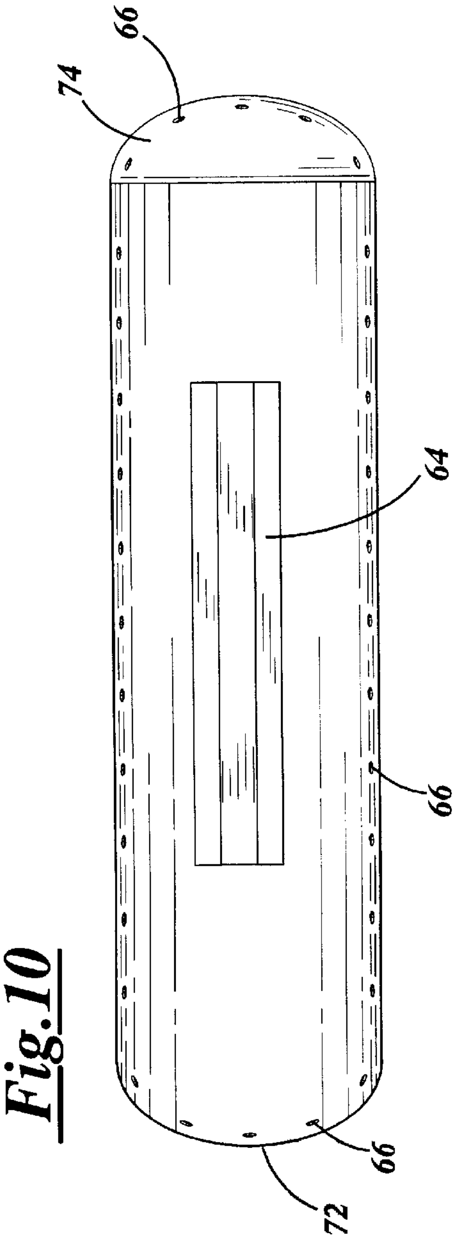
FIG. 10 is a top plan view of the dispenser of the type shown in FIG. 6.

Referring next to FIGS. 6 and 7, an alternate preferred embodiment of the dispenser is shown. The dispenser includes a tubular main body 60, an end cap 62 and a flange or rail 64. A plurality of ports 66 extend through the bottom 68, sides 70, and ends 72 of the dispenser. As described above, the ports 66 allow a slow release of the bacteria contained within the tubular main body 60 into the surrounding body of water. The end cap 62 includes external threading 74, and is adapted for securely screwing onto an open end 76 of the tubular main body 60 (see FIG. 9).

Figure 8:
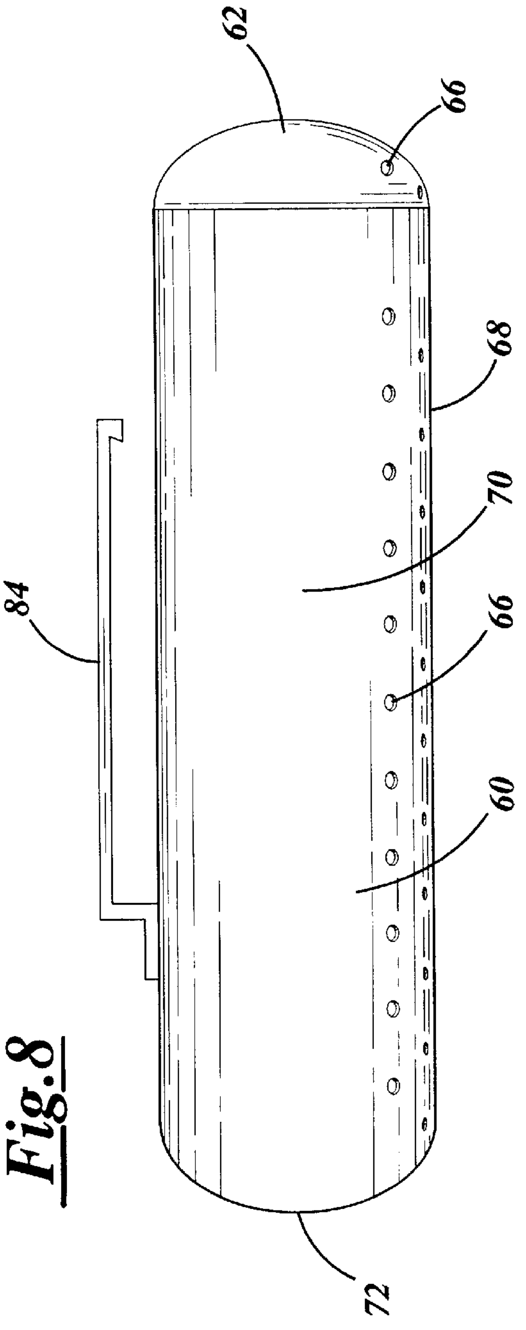
FIG. 8 is a side elevational view of another alternate embodiment of the microorganism dispenser of the present invention.
Figure 11:
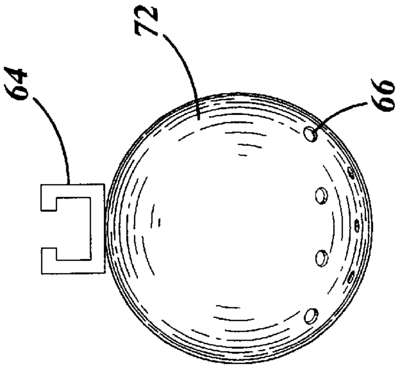
FIG. 11 is an end elevational view of the dispenser of the type shown in FIG. 6.

FIGS. 6, 7, 10, and 11 illustrate the position of the rail 64 on the tubular main body 60 relative to the position of the ports 66 extending through the tubular main body 60. The rail 64 is adapted for sliding over the keel 80 (a portion of which is shown in FIG. 6) of a decoy or other object floating on the surface of a body of water. The rail 64 includes bores 82 extending through the sides of the rail 64, wherein bolts may pass through the bores 82 and fasten to the keel 80. FIG. 8 shows a modified rail structure. In this embodiment, a split rail 84 is shown that slides over a top portion of the keel. A friction fit between the rail 84 and keel 80 secures the dispenser to the floatation device.

Having described the constructional features of the present invention the mode of use will next be presented. The user first selects a pond, lake or other body of fluid to be treated. The growth media, plasticizer, nutrients, and microorganisms suspended in fluid are poured into the open end of the dispenser 10. The cap 14 or 62 is then securely screwed onto the dispenser 10. The dispenser 10 is then placed into the selected body of fluid. The bacteria contained within the dispenser grows on the growth media and later is slowly released out of the growth chamber. In the preferred embodiment, an anchor line or tether may be attached to the lower tab 42, thereby limiting the floatation range of the dispenser 10. In the alternate preferred embodiment the anchor or tether may be attached to the keel 80 of the floatation device.

This invention has been described herein in considerable detail in order to comply with the patent statutes and to provide those skilled in the art with the information needed to apply the novel principles and to construct and use such specialized components as are required. However, it is to be understood that the invention can be carried out by specifically different devices, and that various modifications, both as to the equipment details and operating procedures, can be accomplished without departing from the scope of the invention itself

What is claimed is:

1. A device for culturing and slowly releasing a microorganism contained therein, said device comprising:

(a) a buoyant container having means for suspending a portion of said container above an upper surface of a fluid medium, said container including a growth chamber positionable below the upper surface of said fluid medium, said container having a plurality of conduits extending between an interior surface of the growth chamber and an external surface of the growth chamber, said container further having an opening formed in the portion of the container suspendable above the upper surface of the fluid medium;

(b) microorganisms suspended in a fluid and contained within the growth chamber;

(c) growth media contained in the growth chamber, wherein the microorganisms attach and grow on an external surface of the media; and (d) nutrients contained within the growth chamber.

2. The device as recited in claim 1, wherein the growth media comprises a plurality of spheres manufactured from a polymer.

3. The device as recited in claim 2, wherein a density of the polymer is less than a density of water.

4. The device as recited in claim 2, wherein said container is divided into an upper conical float chamber and a lower spherical growth chamber.

5. The device as recited in claim 4, further including a cap for enclosing the opening formed in the portion of the container suspendable above the upper surface of the fluid medium.

6. The device as recited in claim 4, further including a hook extending from a bottom portion of the spherical growth chamber.

7. A device for culturing and slowly releasing a microorganism contained therein, said device comprising:

(a) a container divided into an upper conical float chamber and a lower spherical growth chamber, said container having a plurality of conduits extending between an interior surface of the growth chamber and an external surface of the growth chamber, said container further having an opening extending through said float chamber, wherein the opening is suspendable above an upper surface of a fluid medium;

(b) microorganisms suspended in a fluid and contained within the growth chamber;

(c) growth media contained in the growth chamber, wherein the microorganisms attach and grow on an external surface of the media; and (d) nutrients contained within the growth chamber.

8. The device as recited in claim 7, wherein the growth media is manufactured from a polymer.

9. The device as recited in claim 8, wherein a density of the polymer is less than a density of water.

10. The device as recited in claim 7, further including a cap for enclosing the opening extending through said float chamber.

11. The device as recited in claim 7, further including a hook extending from a bottom portion of the spherical growth chamber.

* * * * *